United States Patent [19]
Biber

[11] Patent Number: 5,914,771
[45] Date of Patent: Jun. 22, 1999

[54] OPHTHALMOLOGIC VIEWING APPARATUS

[75] Inventor: Klaus Biber, Aalen, Germany

[73] Assignee: Carl-Zeiss-Stiftung, Heidenheim, Germany

[21] Appl. No.: 08/932,054

[22] Filed: Sep. 17, 1997

[30] Foreign Application Priority Data

Sep. 19, 1996 [DE] Germany .............................. 196 38 263

[51] Int. Cl.⁶ ...................................................... A61B 3/10
[52] U.S. Cl. ............................................................ 351/221
[58] Field of Search ..................... 351/205, 213, 351/214, 211, 221

[56] References Cited

U.S. PATENT DOCUMENTS

| | | | |
|---|---|---|---|
| 3,259,041 | 7/1966 | Okajima | 351/207 |
| 4,704,018 | 11/1987 | Takhashi | 351/206 |
| 4,715,704 | 12/1987 | Biber et al. | 351/207 |
| 4,795,250 | 1/1989 | Nakamura et al. | 351/213 |
| 4,998,810 | 3/1991 | Sander et al. | 350/528 |
| 5,126,877 | 6/1992 | Biber | 359/389 |
| 5,555,040 | 9/1996 | Kaneko | 351/221 |

FOREIGN PATENT DOCUMENTS

| | | |
|---|---|---|
| 2512427 | 1/1976 | Germany . |
| 4028605 | 3/1992 | Germany . |
| 4344770 | 6/1995 | Germany . |

*Primary Examiner*—Huy Mai
*Attorney, Agent, or Firm*—Walter Ottesen

[57] ABSTRACT

An ophthalmologic viewing apparatus 1 has a viewing system 23 for viewing the forward eye sections (5, 7, 9) and has an illuminating system 13. The illuminating beam of the illuminating system 13 impinges from the outside on the cornea 5. The viewing apparatus 1 has a light absorber 25 for suppressing the virtual image of the illuminating light source 17, namely, the so-called corneal reflection. The light absorber 25 is in the region of the optical axis 11 of the illuminating system 13 and has dimensions which are small compared to the transverse dimensions of the illuminating beam. The virtual image is formed by the reflection at the convex surface of the cornea 5.

17 Claims, 1 Drawing Sheet

OPHTHALMOLOGIC VIEWING APPARATUS

FIELD OF THE INVENTION

The invention relates to an ophthalmologic viewing apparatus having a viewing system for viewing the forward eye sections and with an illuminating system having an illuminating beam which impinges on the cornea from the outside.

BACKGROUND OF THE INVENTION

In the context of the invention, the cornea, iris and lens correspond to the forward sections of the eye. Fundus cameras for viewing the retina do not belong to the subject matter of the invention because of the basically different optical requirements and conditions.

An ophthalmologic viewing apparatus of the type corresponding to the invention is, for example, the surgical microscope disclosed in German patent publication 4,344,770. The use of this known surgical microscope for removing cataracts takes place with an illuminating beam which impinges on the cornea. A portion of the illuminating beam passes through the cornea in the direction toward the retina and another portion of the illuminating beam is reflected by the cornea which acts as a convex mirror. In this way, a virtual image of the illuminating light source (the so-called corneal reflex) occurs. The illuminating light reaching the retina is then diffusely reflected by the retina and is scattered back to the forward sections of the eye. This light coming from the retina is therefore reddish and passes through the forward eye sections in the direction toward the viewing apparatus. In this way, this reddish light leads to a type of transillumination of the forward sections of the eye. Accordingly, an especially contrast-rich imaging of the forward sections of the eye is possible in the viewing system.

This type of transillumination is also referred to as "red reflex" illumination and requires an illuminating beam of high luminance in order to effect an adequate illumination of the forward sections of the eye. However, this makes the virtual image of the illuminating light source very bright. This image is generated by the reflection of the illuminating radiation on the convex corneal surface and disturbs the viewing of the forward eye sections because of its brightness. This virtual image is characterized as a corneal reflection and can even lead to dazzling of the viewer.

A further viewing apparatus of the type according to the invention is disclosed in U.S. Pat. No. 5,126,877. In this viewing apparatus too, the corneal reflection disturbs the viewing of the forward eye sections. In this viewing apparatus, the illuminating light impinges on the cornea parallel to the optical axis as well as inclined to this axis. The corneal reflection can therefore not only be a problem for a coaxial illumination (0° illumination) but also for illuminating light which impinges on the cornea inclined to the optical axis of the viewing system. The coaxial illumination is especially advantageous for the "red reflection" illumination.

SUMMARY OF THE INVENTION

It is an object of the invention to provide an ophthalmologic viewing apparatus wherein reflections from the cornea are decisively reduced and wherein the forward sections of the eye can nonetheless be brightly illuminated with rich contrast.

The ophthalmologic viewing apparatus includes: a viewing system for viewing an object defined by the forward sections of the eye including the cornea, iris and lens; an illuminating system defining an illuminating optical axis and including a light source for transmitting an illuminating light beam along the axis to the cornea where the illuminating light beam impinges on the cornea from outside of the eye; the illuminating light beam having predetermined dimensions transverse to the illuminating beam axis; and, a light absorber mounted in the region of the illuminating beam axis and having dimensions which are small compared to the transverse dimensions of the illuminating light beam.

More specifically, the dimensions of the light absorber can be less than the transverse dimensions of the illuminating beam at the location of the light absorber by at least a factor of approximately three.

It has been determined that the corneal reflections can be eliminated or at least decisively attenuated with a light absorber of the kind described above. The light absorber is neither itself visible in the viewing field so as to be a disturbance nor does the light absorber noticeably limit the brightness of the viewing field. A suitable position for the light absorber can be determined without difficulty via simple experiments and is dependent upon the details of the particular illuminating system.

On the one hand, it has been assumed that the optimal location for the light absorber is related to the location of the narrowest constriction of the component beam of the illuminating radiation which contributes to imaging the corneal reflection into the viewing system. However, experiments have, on the other hand, shown that the light absorber can be mounted in a relatively wide region of the illuminating system without its effect being diminished; that is, the effect of eliminating the influence caused by corneal reflections.

The invention can be made more clear by a comparison to the viewing apparatus known and disclosed in U.S. Pat. No. 4,715,704.

In the viewing apparatus shown in U.S. Pat. No. 4,715,704, an annular diaphragm can be pivoted into the beam path of the viewing system at a location conjugated to the object plane in order to protect the retina of the eye of the patient under observation. The central opaque disc of this annular diaphragm shades the cornea in such a manner that no illuminating radiation whatsoever reaches the retina of the eye of the patient via the eye pupil. In addition, the central opaque disc of the annular diaphragm is imaged into the viewing field and is clearly viewable in the viewing field.

Furthermore, the central shading of the forward eye sections leads to an illumination which is inadequate for the many applications. This central shading is effected by the annular diaphragm. With this state of the art, the corneal reflection can be suppressed but only at the cost of a disturbing imaging of the central disc of the annular diaphragm into the viewing field and a reduction of the intensity of illumination and therefore of the viewing quality.

In contrast to the above, the light absorber of the ophthalmologic viewing apparatus of the invention generates no apparent shading and has dimensions so small that it always makes possible an adequate illumination for conventional light sources.

The essence of the invention is also shown by the differences between the invention and an ocular fundus camera disclosed in U.S. Pat. No. 3,259,041.

In this ocular fundus camera, and to suppress corneal reflections, an annular diaphragm coacts with an aperture diaphragm in the viewing system in such a manner that illuminating light, which is reflected at the cornea, cannot reach the viewing system. The annular diaphragm is in the illuminating system at a position conjugated to the cornea. The way the corneal reflections are eliminated in an ocular fundus camera thereby permits exclusively viewing the ocular fundus. Viewing the forward sections of the eye is precluded because a sharp image of the annular diaphragm arises on the cornea and this image prevents an adequate illumination of the forward sections of the eye.

It has been shown to be especially advantageous to mount the light absorber on the optical axis of the illuminating system outside of a region conjugated to the object plane. The object plane can lie in any desired region of the forward eye sections depending upon the viewing purpose. With this arrangement of the light absorber, a sharp imaging of the light absorber into the viewing field of the ophthalmologic viewing apparatus and therefore an unwanted influencing of the viewing is avoided.

For an illuminating field diaphragm, which is conjugated to the surface of the cornea, a sharp imaging of the light absorber in the viewing field is especially prevented when the light absorber is mounted on the optical axis of the illuminating system at a spacing from the illuminating-field diaphragm.

Light absorbers having dimensions of less than approximately 2 mm (preferably less than approximately 1 mm) have been shown to be especially suitable. Excellent results can be obtained up to the region of a few tenths of a millimeter. In this way, the forward sections of the eye can be viewed practically with unreduced illuminating intensity without unwanted influence because of a very bright corneal reflection. With these small dimensions, it is advantageous to mount the light absorber on an opaque carrier plate.

Advantageously, the light absorber is completely opaque. In this way, the corneal reflection can be suppressed with very small dimensions of the light absorber. However, even light absorbers which are partially light transmissive can suppress the corneal reflection as has been established by experiment.

The optimal location of the light absorber can be adjusted individually for each patient when the light absorber is mounted so as to be axially and/or laterally displaceable in the illuminating system.

In a further embodiment of the invention, the light absorber can be removed from the illuminating beam path of the illuminating system. In this way, the ophthalmologic viewing apparatus can easily be used for viewing tasks outside of ophthalmology.

In the event that the illuminating beam impinges on the cornea at an angle between approximately 0° to approximately 4° to the optical axis of the viewing system, the invention can be used especially effectively with an optimal "red reflex" illumination for a contrast-rich imaging of the forward sections of the eye.

For imaging a light-conductor end face on the retina of the eye to be viewed, the illuminating system can include a lens arrangement having an aspherical lens mounted forward of the light-conductor end face. The light absorber is mounted between the light-conductor end face and the aspherical lens. In this way, the suppression of the corneal reflection is very effective even with an exceptionally small light absorber, for example, a black point. The basis of this condition is possibly that, for this configuration of the illuminating system, the constriction (that is, the pupil) of the beam, which contributes to the imaging of the corneal reflection image into the viewing system, lies between the light-conductor end face and the aspheric lens and has an especially small diameter.

When the illuminating system includes at least one illuminating deflecting mirror, which deflects the illuminating beam in the direction toward the cornea, the illuminating system is substantially separated from the viewing beam path. In this way, the possible and favorable locations for installing the light absorber are accessible without intervening in the viewing system.

For this embodiment, the illuminating system can further include a diaphragm, which is displaceable parallel to the illuminating deflecting mirror. With a diaphragm of this kind and in order to increase contrast, a phase-contrast generating effect of the illuminating deflecting mirror can be amplified further without being affected by the corneal reflection.

The location of the light absorber and the illuminating angle can be adjusted optimally with respect to each other when at least one illuminating deflecting mirror is displaceably mounted orthogonally to the optical axis of the viewing system.

According to still another advantageous embodiment of the invention, the illuminating system has a variable illuminated field with a variable luminescence. For example, similar to U.S. Pat. No. 4,998,810, this can be achieved for a small illuminated field with a large illuminating pupil and, for a large illuminated field, by a small illuminating pupil. The illuminating pupil is the image of the light source on the illuminating deflecting mirror(s) and, correspondingly, is the image of the light source on the retina. In this way, a constant brightness is achieved on the retina and therefore also a certain measure of protection of the retina against excessive radiation load.

The ophthalmologic viewing apparatus of the invention is especially advantageous as a surgical microscope for cataract removal because here, the corneal reflection greatly negatively influences the exceptionally important recognition of details in the presence of red-reflection illumination. It is here advantageous when an automatic centering of the viewing beam path on the corneal reflection center compensates for greater movements of the eye to be investigated.

BRIEF DESCRIPTION OF THE DRAWINGS

The invention will now be described with reference to the single FIGURE (FIG. 1) of the drawing which shows a schematic cross section of the viewing apparatus according to an embodiment of the invention.

DESCRIPTION OF THE PREFERRED EMBODIMENTS OF THE INVENTION

Figure 1:
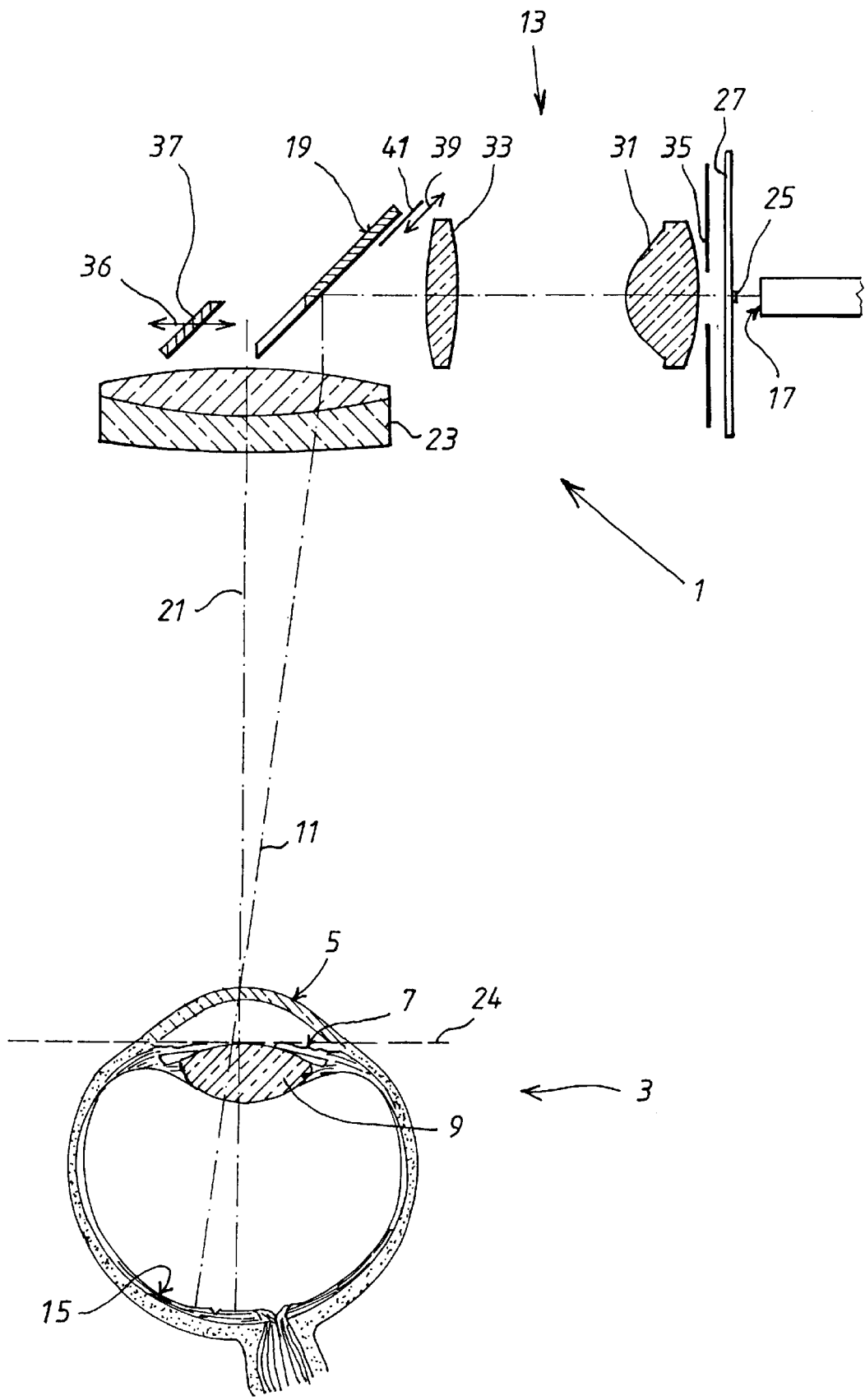

In FIG. 1, the viewing apparatus is identified by reference numeral 1 and the eye to be investigated is identified by reference numeral 3. The viewing apparatus 1 is configured especially for viewing the forward sections of the eye 3, that is, for example, the cornea 5, the iris 7 or the lens 9.

The forward eye sections (5, 7 or 9) are illuminated with the aid of an illuminating system 13 having an optical axis 11. The illuminating beam of the illuminating system 13 impinges from externally of the eye 3 on the cornea 5. The illuminating light can pass through the forward eye sections and impinge upon the retina 15 of the eye 3 and be reflected by the retina 15 and illuminate the forward eye sections in transmission.

For this illuminating light, which impinges from externally on the cornea 5, the problem occurs that a virtual image of the illuminating light source 17 (or of the illuminating deflecting mirror 19 and of the illuminating deflecting mirror 37 explained further below) occurs and disturbs the viewing.

The virtual image is caused by the reflection at the corneal surface which operates as a convex mirror.

The virtual image is characterized as a corneal reflection. In order to eliminate the imaging of this virtual image in the viewing system or to at least attenuate this virtual image in this intensity so that it does not dazzle the viewer, a light absorber 25 is mounted in the region of the optical axis 11 of the illuminating system. The dimensions of the light absorber 25 are small compared to the transverse dimensions of the illuminating beam. The viewing system includes an optical axis 21 and a main objective 23. This light absorber 25 advantageously has dimensions less than approximately 1 mm and is held on a light-transmissive carrier plate 27. Very good results are obtained with respect to suppression of corneal reflection even with dimensions in the order of magnitude of a tenth of a millimeter (1/10 mm).

The transverse dimensions of the viewing beam are determined by the opening range of an illuminating field diaphragm 35 in the viewing apparatus shown. The illuminating field diaphragm 35 is displaceable together with aspheric lens 31 and a convex lens 33 in order to vary the illuminating field. The lenses 31 and 33 and the illuminating field diaphragm 35 are displaced in such a manner that the ophthalmologic viewing apparatus exhibits a variable illuminating field with constant luminescence.

In the embodiment shown, the light absorber 25 is arranged on a transparent carrier plate 27 and is mounted outside of the region of the illuminating system 13 conjugated to the cornea 5; that is, the light absorber 25 is not mounted at the location of the illuminating field diaphragm 35. The light absorber 25 is mounted between the illuminating light source, which is configured as a light-conductor end face 17, and the illuminating field diaphragm 35. The light absorber 25 can however be mounted between the illuminating field diaphragm 35 and the aspheric lens 31 or between the aspheric lens 31 and the lens 33. The most suitable locations for the light absorber 25 can be determined quickly from simple experiments.

In addition to the deflecting mirror 19, an illuminating deflecting mirror 37 is provided with which an incidence of the illuminating light on the cornea 5 parallel to the optical axis 21 of the viewing system can take place for a red-reflection illumination. The illuminating deflecting mirror 37 is displaceable in the direction of the double arrow 36 orthogonally to the optical axis 21 of the viewing system. Details of this illuminating deflecting mirror 37 are disclosed in U.S. Pat. No. 5,126,877 incorporated herein by reference.

To increase contrast, a diaphragm 41 can be displaced into the illuminating beam. This diaphragm 41 is displaceable parallel to the illuminating deflecting mirror 19 in the direction of the double arrow 39.

It is understood that the foregoing description is that of the preferred embodiments of the invention and that various changes and modifications may be made thereto without departing from the spirit and scope of the invention as defined in the appended claims.

What is claimed is:

1. An ophthalmologic viewing apparatus comprising:

a viewing system for viewing an object defined by the forward sections of the eye including the cornea, iris and lens;

an illuminating system defining an illuminating optical axis and including a light source for transmitting an illuminating light beam along said axis to said cornea where said illuminating light beam impinges on said cornea from outside of said eye;

said illuminating light beam having predetermined dimensions transverse to said illuminating optical axis; and, a light absorber mounted in the region of said illuminating optical axis and having dimensions which are small compared to said transverse dimensions of said illuminating light beam;

said object defining an object plane and said illuminating system including a lens assembly for defining a region conjugated to said object plane; and, said light absorber being mounted on said illuminating optical axis outside said region.

2. The ophthalmologic viewing apparatus of claim 1, said illuminating system including an illuminating field diaphragm mounted on said illuminating optical axis downstream of said light source; and, said light absorber being mounted on said illuminating optical axis spaced from said illuminating field diaphragm.

3. The ophthalmologic viewing apparatus of claim 1, said light absorber having dimensions less than 2 mm.

4. The ophthalmologic viewing apparatus of claim 1, said light absorber having dimensions less than 1 mm.

5. The ophthalmologic viewing apparatus of claim 1, said illuminating system including a transparent carrier plate and said light absorber being mounted on said transparent carrier plate.

6. The ophthalmologic viewing apparatus of claim 1, said light absorber being fully opaque.

7. The ophthalmologic viewing apparatus of claim 1, said light absorber being partially light transmissive.

8. The ophthalmologic viewing apparatus of claim 1, said light absorber being axially or laterally displaceable.

9. The ophthalmologic viewing apparatus of claim 1, said light absorber being both axially and laterally displaceable.

10. The ophthalmologic viewing apparatus of claim 1, said light absorber being removable from said illuminating system.

11. The ophthalmologic viewing apparatus of claim 1, said illuminating system including optical elements mounted on said illuminating optical axis for causing said illuminating light beam to impinge on said cornea at an angle between approximately 0° and 4°.

12. The ophthalmologic viewing apparatus of claim 1, wherein said eye includes a retina; said illuminating system further including a light conductor having an end face defining said light source; and, a lens assembly mounted on said illuminating optical axis for imaging said end face on said retina; said lens assembly including an aspherical lens mounted forward of said end face; and, said light absorber being mounted between said end face and said aspheric lens.

13. The ophthalmologic viewing apparatus of claim 12, said illuminating system further including at least one deflecting mirror for deflecting said illuminating light beam onto said cornea.

14. The ophthalmologic viewing apparatus of claim 13, said illuminating system further including at least one diaphragm displaceable parallel to said deflecting mirror.

15. The ophthalmologic viewing apparatus of claim 14, said viewing system defining a viewing optical axis; and, said illuminating system further including at least one deflecting mirror mounted so as to be displaceable orthogonally to said viewing optical axis.

16. The ophthalmologic viewing apparatus of claim 1, wherein said illuminating system has a variable illuminating field having a variable illuminating density; and, said illuminating field is smaller for a larger illuminating pupil and said illuminating field is larger for a smaller illuminating pupil.

17. The ophthalmologic viewing apparatus of claim 1, wherein said apparatus is a surgical microscope configured for cataract removal.

\* \* \* \* \*